US012729388B2

(12) United States Patent
Hu et al.

(10) Patent No.: US 12,729,388 B2
(45) Date of Patent: Sep. 8, 2026

(54) METHODS AND SYSTEMS FOR PRODUCING CELLULOSIC ETHANOL BY BIOMASS SACCHARIFICATION AND FERMENTATION

(71) Applicant: ZHEJIANG HUAKANG PHARMACEUTICAL CO., LTD., Quzhou (CN)

(72) Inventors: Changhui Hu, Quzhou (CN); Jiaxing Luo, Quzhou (CN); Mian Li, Quzhou (CN); Chengjun Liao, Quzhou (CN); Wulong Yang, Quzhou (CN); Liangcong Yan, Quzhou (CN); Ni Zhen, Quzhou (CN); Lanlan Chen, Quzhou (CN)

(73) Assignee: ZHEJIANG HUAKANG PHARMACEUTICAL CO., LTD., Quzhou (CN)

( * ) Notice: Subject to any disclaimer, the term of this patent is extended or adjusted under 35 U.S.C. 154(b) by 559 days.

(21) Appl. No.: 18/348,319

(22) Filed: Jul. 6, 2023

(65) Prior Publication Data

US 2023/0348940 A1 Nov. 2, 2023

Related U.S. Application Data

(63) Continuation-in-part of application No. PCT/CN2022/092087, filed on May 10, 2022.

(30) Foreign Application Priority Data

Nov. 25, 2021 (CN) ......................... 202111416152.6

(51) Int. Cl.

*C12P 7/10* (2006.01)
*C12M 1/00* (2006.01)

(Continued)

(52) U.S. Cl.

CPC ............... *C12P 7/10* (2013.01); *C12M 21/04* (2013.01); *C12M 23/40* (2013.01); *C12M 23/58* (2013.01);

(Continued)

(58) Field of Classification Search

None

See application file for complete search history.

(56) References Cited

U.S. PATENT DOCUMENTS 4,321,328 A 3/1982 Hoge
4,376,163 A 3/1983 Ehnström (Continued)

FOREIGN PATENT DOCUMENTS

CN 101899478 A 12/2010
CN 104611381 A 5/2015

(Continued)

OTHER PUBLICATIONS

Sun, Yadong et al., Study on Conversion Process for Furfural Residue Manufacture to Ethanol by Simultaneous Saccharification and Fermentation, Modern Chemical Industry, 28(12): 48-52, 2008.

(Continued)

*Primary Examiner* — John J Figueroa
(74) *Attorney, Agent, or Firm* — METIS IP LLC

(57) ABSTRACT

A system and method for producing cellulosic ethanol by biomass saccharification and fermentation is provided. The system includes a first reactor configured to carry out an enzymatic hydrolysis reaction of a biomass feedstock, a second reactor configured to carry out a fermentation reaction of the biomass feedstock, and a collection tank configured to collect the cellulosic ethanol. The first reactor and second reactor are provided with an enzymatic hydrolysis dosing pipe and a fermentation dosing pipe, respectively. An outlet of the first reactor is connected to an inlet of the (Continued)

second reactor through a fermentation pipe. An outlet of the second reactor is connected to an inlet of the first reactor through a discharge pipe that is provided with a first discharge pipe configured to discharge material from the second reactor. The first reactor is connected to an inlet of the collection tank through an ethanol pipe.

19 Claims, 5 Drawing Sheets

(51) Int. Cl.
*C12M 1/107* (2006.01)
*C12M 1/34* (2006.01)
*C12N 9/42* (2006.01)
*C12P 7/14* (2006.01)

(52) U.S. Cl.
CPC ............ *C12M 41/12* (2013.01); *C12M 47/12* (2013.01); *C12N 9/2437* (2013.01); *C12P 7/14* (2013.01); *C12Y 302/01004* (2013.01)

(56) References Cited

U.S. PATENT DOCUMENTS 9,034,620 B2 * 5/2015 Narendranath ........... C12P 7/10 435/165
9,193,982 B2 * 11/2015 Sjoede ..................... C13K 1/02
9,663,807 B2 * 5/2017 Narendranath .......... C13K 1/02
2012/0040423 A1 2/2012 Grundberg
2013/0217074 A1 * 8/2013 Sjoede ..................... C08H 6/00 435/162
2014/0234911 A1 * 8/2014 Narendranath ........ C12M 21/12 435/99
2015/0240268 A1 8/2015 Aymard et al.
2017/0225098 A1 8/2017 Schultz
2018/0363017 A1 * 12/2018 Tolan ..................... C12M 45/09

FOREIGN PATENT DOCUMENTS

CN 105624205 A 6/2016
CN 105624206 A 6/2016
CN 105713931 A 6/2016
CN 113913471 A 1/2022
CN 216378252 U 4/2022
WO 2010110448 A1 9/2010

OTHER PUBLICATIONS

Wang, Liang et al., High Titer Ethanol Production from an Atmospheric Glycerol Autocatalytic Organosolv Pretreated Wheat Straw, Chinese Journal of Biotechnology, 31(10): 1468-1483, 2015.
Zhao, Jing et al., Study on Enzymatic Hydrolysis of Corncob for Ethanol Production, Chemistry and Industry of Forest Products, 27(4): 7-10, 2007.
The Extended European Search Report in European Application No. 22897056.2 mailed on Jan. 5, 2026, 11 pages.
Decision to Grant a Patent in Japanese Application No. 2023-549920 mailed on Apr. 9, 2025, 6 pages.
International Search Report in PCT/CN2022/092087 mailed on Aug. 23, 2022, 7 pages.

* cited by examiner

METHODS AND SYSTEMS FOR PRODUCING CELLULOSIC ETHANOL BY BIOMASS SACCHARIFICATION AND FERMENTATION

CROSS-REFERENCE TO RELATED APPLICATIONS

This application is a continuation-in-part application of International Application No. PCT/CN2022/092087 filed on May 10, 2022, which claims the priority of the Chinese Patent Application No. 202111416152.6, filed on Nov. 25, 2021, the entire contents of each of which are incorporated herein by reference.

TECHNICAL FIELD

The present disclosure relates to a technical field of cellulosic ethanol production, and in particular to systems and methods for producing cellulosic ethanol by biomass saccharification and fermentation.

BACKGROUND

The development of sustainable and pollution-free energy sources is a technological development trend. A large amount of lignocellulosic waste such as straw and corncobs are produced every year in agricultural production. Main components in lignocellulosic material are cellulose, hemicellulose, lignin, and a small amount of ash. The cellulose may be hydrolyzed by cellulase to obtain glucose. The glucose may be used to produce cellulosic ethanol through biological fermentation. The cellulosic ethanol may be used as a clean fuel.

At present, there are many bottlenecks in the process of producing the cellulosic ethanol from a biomass feedstock. A most widely used process is simultaneous saccharification and fermentation (SSF), but the SSF process cannot ensure the optimal conditions for enzymatic hydrolysis and fermentation at the same time. Besides, the produced cellulosic ethanol has a certain inhibitory effect on the cellulase, thereby affecting the enzymatic hydrolysis and fermentation efficiency.

Therefore, it is desired to provide a system and method for producing the cellulosic ethanol by biomass saccharification and fermentation, thereby improving the production cellulosic ethanol.

SUMMARY

One or more embodiments of the present disclosure provide a system for producing cellulosic ethanol by biomass saccharification and fermentation. The system may include a first reactor, a second reactor, and a collection tank. The first reactor may be configured to carry out an enzymatic hydrolysis reaction of a biomass feedstock. The second reactor may be configured to carry out a fermentation reaction of the biomass feedstock. The collection tank may be configured to collect the cellulosic ethanol produced from the fermentation reaction of the biomass feedstock. The first reactor may be provided with an enzymatic hydrolysis dosing pipe. The second reactor may be provided with a fermentation dosing pipe. An outlet of the first reactor may be connected to an inlet of the second reactor through a fermentation pipe. An outlet of the second reactor may be connected to an inlet of the first reactor through a discharge pipe. A first discharge pipe may be provided on the discharge pipe and configured to discharge material from the second reactor. The first reactor may be connected to an inlet of the collection tank through an ethanol pipe. The first reactor may be provided with an insulation layer for heating and keeping the first reactor warm.

One or more embodiments of the present disclosure provide a method for producing cellulosic ethanol by biomass saccharification and fermentation. The method may be implemented by the aforementioned system for producing cellulosic ethanol by biomass saccharification and fermentation. The method may include a dosing step, an enzymatic hydrolysis reaction step, a fermentation reaction step, a cellulosic ethanol production step, and repeat steps. In the dosing step, the biomass feedstock is added to a citric acid buffer solution, and cellulase is added to form a mixture. Further, the prepared mixture is dosed to the first reactor through the enzymatic hydrolysis dosing pipe. In the enzymatic hydrolysis reaction step, the mixture is carried out an enzymatic hydrolysis reaction by maintaining a temperature of the first reactor at an enzymatic hydrolysis reaction temperature through the insulation layer. In the fermentation reaction step, the material (i.e., the mixture) after the enzymatic hydrolysis reaction in the first reactor is transported to the second reactor through the fermentation pipe, and then fermentation strains are added to the second reactor through the fermentation dosing pipe. Further, the material after the enzymatic hydrolysis reaction is carried out a fermentation reaction by maintaining a temperature of the second reactor at a fermentation temperature. In the cellulosic ethanol production step, after the fermentation reaction is completed, the material after the fermentation reaction in the second reactor is transported to the first reactor through the discharge pipe. The cellulosic ethanol in the material after the fermentation reaction is evaporated into cellulosic ethanol vapors in the first reactor, and the cellulosic ethanol vapors flow into the collection tank through the ethanol pipe and are condensed into the cellulosic ethanol. In the repeat steps, the enzymatic hydrolysis reaction step, the fermentation reaction step, and the cellulosic ethanol production step are repeated. The material is respectively circulated multiple cycles in the first reactor and the second reactor, and after the circulation is completed in the second reactor, the material is discharged from the system through the first discharge pipe.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

Figure 1:
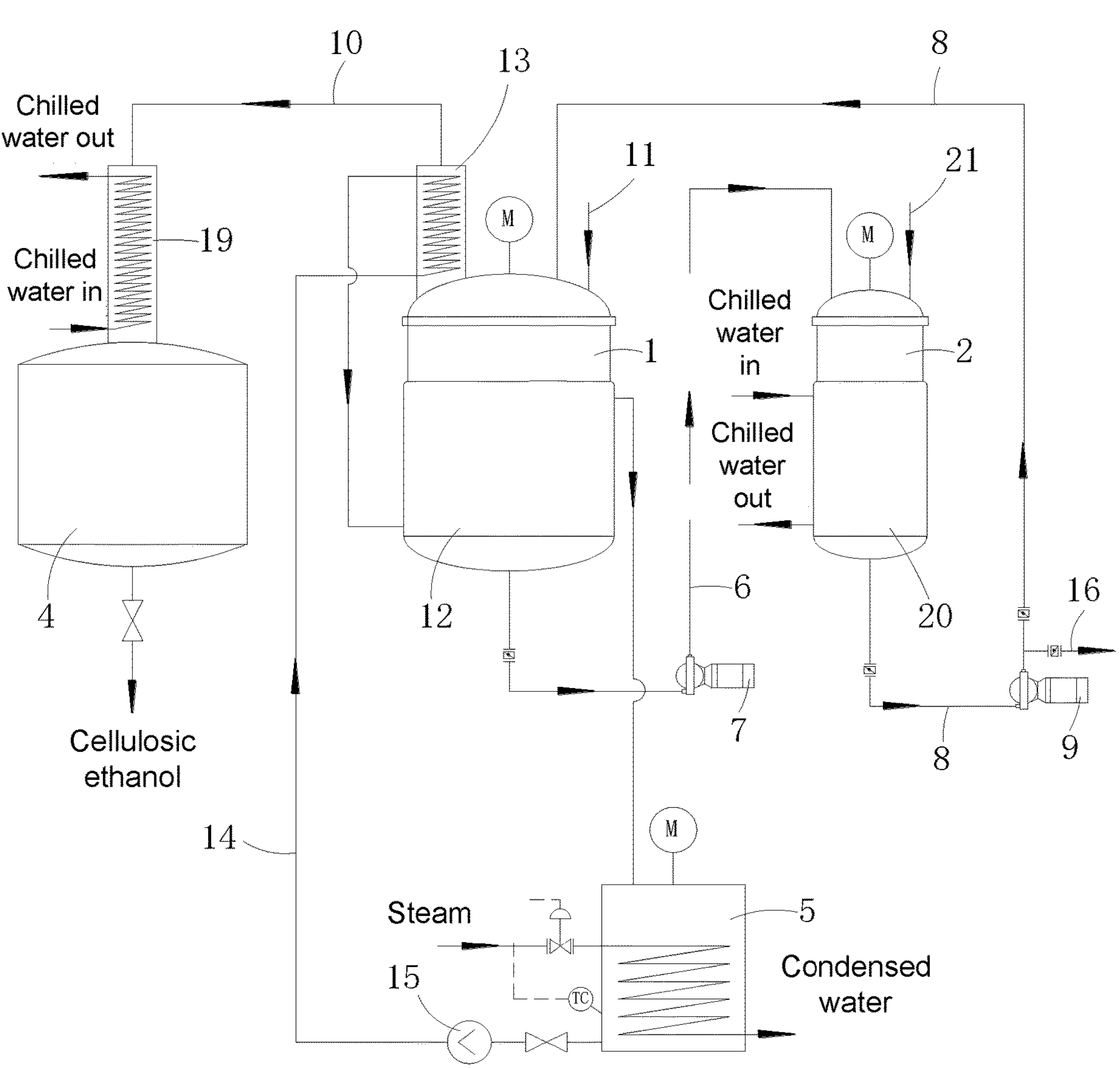
FIG. 1 is a schematic diagram illustrating an exemplary structure of a system for producing cellulosic ethanol by biomass saccharification and fermentation according to some embodiments of the present disclosure.

In order to more clearly illustrate the technical solutions related to the embodiments of the present disclosure, a brief introduction of the drawings referred to the description of the embodiments is provided below. Obviously, the drawings described below are only some examples or embodiments of the present disclosure. Those having ordinary skills in the art, without further creative efforts, may apply the present disclosure to other similar scenarios according to these drawings. Unless obviously obtained from the context or the context illustrates otherwise, the same numeral in the drawings refers to the same structure or operation.

It should be understood that "system", "device", "unit" and/or "module" as used herein is a method for distinguishing different components, elements, parts, portions, or assemblies of different levels. However, the words may be replaced by other expressions if other words can achieve the same purpose.

As indicated in the disclosure and claims, the terms "a", "an", "an" and/or "the" are not specific to the singular form and may include the plural form unless the context clearly indicates an exception. Generally speaking, the terms "comprising" and "including" only suggest the inclusion of clearly identified steps and elements, and these steps and elements do not constitute an exclusive list, and the method or device may also contain other steps or elements.

The flowcharts used in the present disclosure may illustrate operations that systems implement according to some embodiments of the present disclosure. It is to be expressly understood, the operations of the flowcharts may be implemented not in order. Conversely, the operations may be implemented in inverted order, or simultaneously. Moreover, one or more other operations may be added to the flowcharts. One or more operations may be removed from the flowcharts.

At present, there are still many bottlenecks in a process of producing cellulosic ethanol from a biomass feedstock. The process of producing cellulosic ethanol mainly includes pretreatment of the biomass feedstock, cellulase enzymatic hydrolysis, and glucose fermentation. For the cellulase enzymatic hydrolysis and saccharification, the challenge is an inhibitory effect of produced glucose in a process of increasing a high solid content of an enzymatic hydrolysis system, especially in a later stage of enzymatic hydrolysis, a concentration of released monomeric glucose increases, which exerts a stronger inhibitory effect on cellulase activity, thereby leading to a decrease in overall enzymatic hydrolysis efficiency and in conversion efficiency of cellulose by enzymatic hydrolysis.

To address the issue of the product inhibitory during enzymatic hydrolysis, simultaneous saccharification and fermentation (SSF) enables microbial fermentation of glucose into cellulosic ethanol when the glucose is released during the cellulase enzymatic hydrolysis, thus alleviating the product inhibitory. The cellulase enzymatic hydrolysis and the glucose fermentation are combined into one process. However, there are still some problems. At present, an optimal reaction temperature for common and efficient commercial cellulase is usually above 45° C., while an optimal fermentation temperature for common ethanol fermentation strains, such as brewing yeast, is 35° C. At 45° C., the ethanol fermentation strains not only cannot grow to produce ethanol, but also tend to apoptosis. The SSF process cannot ensure the optimal conditions for the enzymatic saccharification and the fermentation at the same time. Besides, the produced cellulosic ethanol has a certain inhibitory effect on the cellulase, thereby affecting the enzymatic hydrolysis and fermentation efficiency.

Therefore, some embodiments of the present disclosure provide a system and method for producing the cellulosic ethanol by biomass saccharification and fermentation, which integrates the cellulose enzymatic hydrolysis process and the ethanol fermentation process into an intermittent enzymatic hydrolysis and fermentation process to address the issue of the activity inhibition of the cellulase caused by the produced glucose and ethanol, thereby improving the production of the cellulosic ethanol.

FIG. 1 is a schematic diagram illustrating an exemplary structure of a system 100 for producing cellulosic ethanol by biomass saccharification and fermentation according to some embodiments of the present disclosure. In some embodiments, arrows in the FIG. 1 indicate directions of travel of materials (e.g., a biomass feedstock, steam, chilled water, condensed water, strains, ethanol, etc.) in the system.

In some embodiments, as shown in FIG. 1, the system 100 may include a first reactor 1, a second reactor 2, and a collection tank 4. A reactor (e.g., the first reactor 1, second reactor 2) refers to a device for performing a chemical reaction during chemical production or experiment. The first reactor 1 may be configured to carry out an enzymatic hydrolysis reaction of the biomass feedstock. The second reactor 2 may be configured to carry out a fermentation reaction of the biomass feedstock. The collection tank 4 may be configured to collect the cellulosic ethanol produced from the fermentation reaction of the biomass feedstock. The collection tank 4 refers to a container for collecting substances generated by a chemical reaction.

In some embodiments, the first reactor 1 is provided with an enzymatic hydrolysis dosing pipe 11, and the second reactor 2 is provided with a fermentation dosing pipe 21. An outlet of the first reactor 1 is connected to an inlet of the second reactor 2 through a fermentation pipe 6. An outlet of the second reactor 2 is connected to an inlet of the first reactor 1 through a discharge pipe 8. In some embodiments, a first discharge pipe 16 is provided on the discharge pipe 8 and configured to discharge material from the second reactor 2. In some embodiments, the first reactor 1 is connected to an inlet of the collection tank 4 through an ethanol pipe 10, and the first reactor 1 is provided with an insulation layer 12 for heating and keeping the first reactor 1 warm.

In some embodiments, by setting the first reactor 1, the second reactor 2, and the collection tank 4, the biomass feedstock is subjected to the enzymatic hydrolysis reaction in the first reactor 1, the biomass feedstock after the enzymatic hydrolysis reaction is subjected to the fermentation reaction in the second reactor 2, and then the produced cellulosic ethanol is extracted in the first reactor 1. After fermentable glucose accumulates at a certain concentration, the glucose is fermented to produce the cellulosic ethanol, thereby addressing the issue of the inhibitory of the glucose accumulation on the cellulase activity. Multiple cycles processes of the enzymatic hydrolysis, the fermentation, and the ethanol extraction are carried out on the biomass feedstock at intervals, thereby reducing the inhibitory effect of the ethanol accumulation on the hydrolysis and fermentation processes and improving the conversion rate of the cellulosic ethanol.

In some embodiments, a first diaphragm pump 7 is provided on the fermentation pipe 6, a second diaphragm pump 9 is provided on the discharge pipe 8, and the first discharge pipe 16 is located downstream of the second diaphragm pump 9. A diaphragm pump (e.g., the first diaphragm pump 7, the second diaphragm pump 9) may agitate back and forth through a diaphragm plate to change a volume of a working chamber to suction and discharge liquid.

In some embodiments, the first diaphragm pump 7 provided on the fermentation pipe 6 may transport the material that has undergone the enzymatic hydrolysis reaction to the second reactor 2. In some embodiments, the first discharge pipe 16 located downstream of the second diaphragm pump 9 may discharge the material in the second reactor 2 from the system under an action of the second diaphragm pump 9. In some embodiments, the material not discharged through the first discharge pipe 16 may be transported to the first reactor 1 through the discharge pipe 8 under an action of the second diaphragm pump 9.

In some embodiments, a coil insulation device 13 is provided at a connection between the first reactor 1 and the ethanol pipe 10. The coil insulation device 13 refers to a device being coiled around a pipe for heating and insulating the pipe. In some embodiments, the coil insulation device 13 and the insulation layer 12 may be respectively connected to a hot water tank 5 through a hot water pipe 14, and a centrifugal pump 15 is provided on the hot water pipe 14.

In some embodiments, the coil insulation device 13 may be configured to ensure that evaporated cellulosic ethanol vapors in the first reactor 1 do not condense and may thus be better transported to the collection tank 4. In some embodiments, hot water in the hot water tank 5 may enter the coil insulation device 13 and the insulation layer 12 by an action of the centrifugal pump 15. Therefore, by controlling a temperature of the hot water, temperatures of the first reactor 1 and the coil insulation device 13 may be regulated to maintain a required temperature in the first reactor 1, thereby ensuring that the evaporated cellulosic ethanol vapors, after entering the ethanol pipe 10, do not condense and flow back into the first reactor 1.

In some embodiments, an ethanol freezing device 19 is provided at a connection between an upper part of the collection tank 4 and the ethanol pipe 10, and the ethanol freezing device 19 is configured to condense the cellulosic ethanol vapors by cooling down. In some embodiments, the ethanol freezing device 19 may include a chilled water pipe coiled around the ethanol pipe 10. The cellulosic ethanol vapors may be cooled down and condensed by passing lower-temperature chilled water in the chilled water pipe, so that the cellulosic ethanol may be collected in the collection tank 4. As used herein, the chilled water refers to water that has been chilled and cooled.

In some embodiments, a fermentation cooling device 20 is provided outside the second reactor 2 and configured to cool fermenting material inside the second reactor 2.

In some embodiments, the optimal reaction temperature for the cellulase is typically above 45° C., while the optimal fermentation temperature for the ethanol fermentation strains, such as the brewing yeast, is 35° C. The fermentation cooling device 20 reduces a temperature of the material after the enzymatic hydrolysis reaction to a temperature required for the fermentation reaction.

In some embodiments, a stirring device (not shown in the figure) may be respectively provided in the first reactor 1 and the second reactor 2. By setting the stirring devices in the first reactor 1 and the second reactor 2, the enzymatic hydrolysis reaction and the fermentation reaction may be sufficiently carried out.

In some embodiments, a same batch of biomass material may carry out a single-circulation flow between the first reactor 1 and the second reactor 2. It should be noted that the single-circulation is relative to a double-circulation described below. The single-circulation may correspond to a situation where only one batch of material is circulated in the system. For example, the biomass feedstock is added to the first reactor 1 for the enzymatic hydrolysis reaction, the material after the enzymatic hydrolysis reaction is transported through the fermentation pipe 6 to the second reactor 2 for the fermentation reaction, and then the material after the fermentation reaction is transported back to the first reactor 1 through the discharge pipe 8. The cellulosic ethanol in the material after the fermentation reaction is evaporated into the cellulosic ethanol vapors in the first reactor 1, and the cellulosic ethanol vapors flow into the collection tank 4 through the ethanol pipe 10 to be condensed into the cellulosic ethanol. More descriptions regarding on the flow of the material during producing the cellulosic ethanol may be found in the relevant descriptions below.

Figure 2:
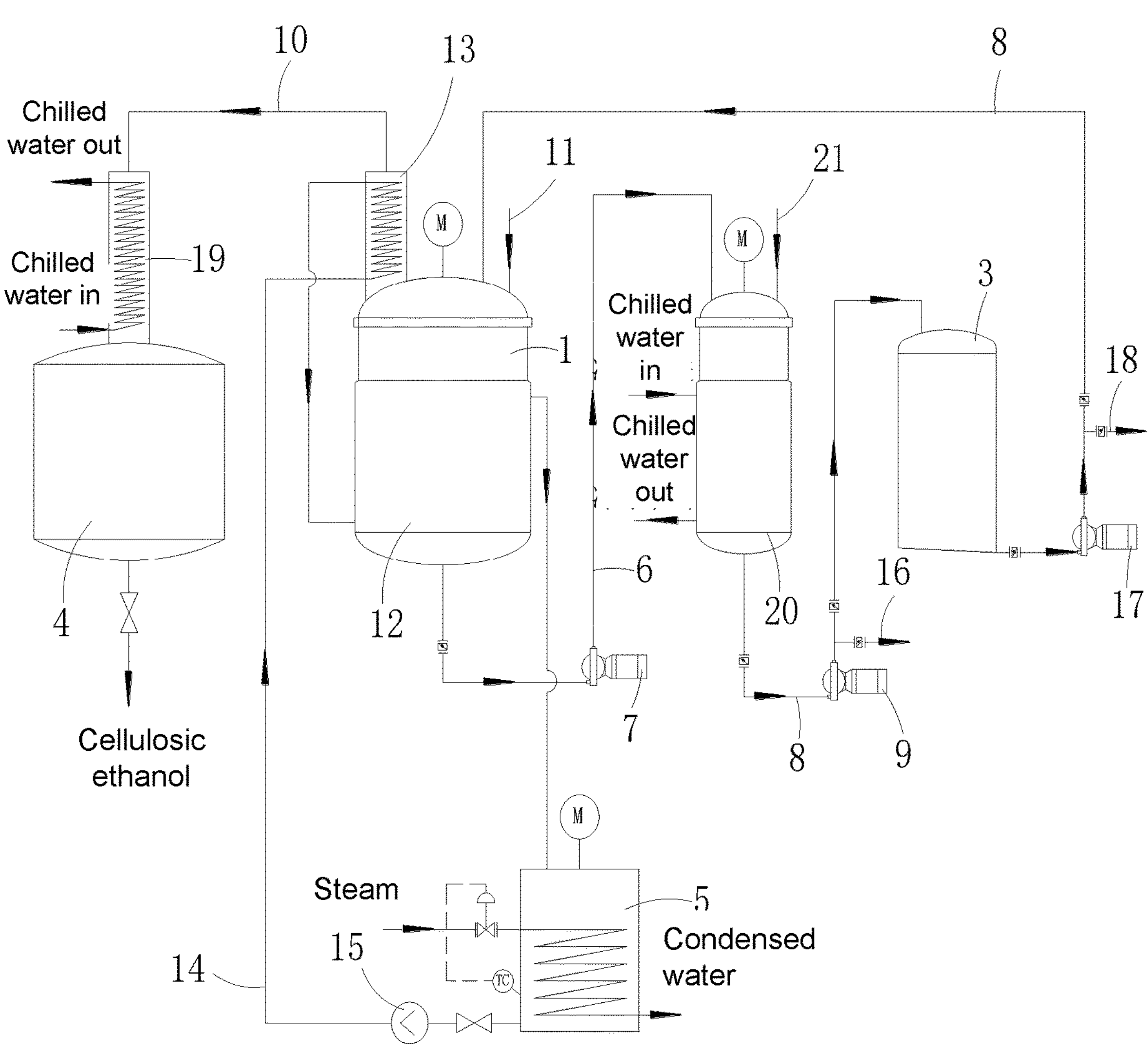
FIG. 2 is a schematic diagram illustrating an exemplary structure of the system for producing cellulosic ethanol by biomass saccharification and fermentation according to some embodiments of the present disclosure.

FIG. 2 is a schematic diagram illustrating an exemplary structure of a system 200 for producing cellulosic ethanol by biomass saccharification and fermentation according to some embodiments of the present disclosure.

In some embodiments, as shown in FIG. 2, the discharge pipe 8 is provided with a storage tank 3, a third diaphragm pump 17, and a second discharge pipe 18. The storage tank 3 is located downstream of the first discharge pipe 16 and configured to store material discharged from the second reactor 2. The second discharge pipe 18 is located downstream of the third diaphragm pump 17. Other structures of the system 200 are the same as or similar to the embodiments shown in FIG. 1, more descriptions regarding these structures may be found in the relevant descriptions in FIG. 1, and not be repeated here.

In some embodiments, due to the addition of the storage tank 3 as a turnover temporary storage tank, two batches of biomass material may be allowed to circulate simultaneously in the system, i.e., the two batches of biomass material may be carried out the double-circulation flow in the first reactor 1 and the second reactor 2 in sequence. For example, a first batch of material may undergo enzymatic hydrolysis in the first reactor 1 and fermentation in the second reactor 2. The first batch of material after the fermentation may be transported to the storage tank 3 for temporary storage. Then, a second batch of material may be added into the first reactor 1 for the enzymatic hydrolysis and the fermentation sequentially. Further, the first batch of material and the second batch of material are sequentially inputted into the first reactor 1 for evaporation to obtain the cellulosic ethanol. More descriptions regarding on the flow of the material during producing the cellulosic ethanol may be found in the relevant descriptions below.

In some embodiments, the system (e.g., the system 100, the system 200) for producing cellulosic ethanol by biomass saccharification and fermentation may further include a detection device (not shown in the figure). The detection device may be configured to detect an amount of the material in the first reactor 1 at a moment when the material starts to be discharged. In some embodiments, the detection device is arranged on an outlet of the first reactor 1. For example, the detection device may be arranged at a connection between the first reactor 1 and the ethanol pipe 10. As another example, the detection device may be arranged at a connection between the first reactor 1 and the fermentation pipe 6. In other embodiments, the detection device may be arranged in the first reactor 1.

In some embodiments, the system may predict a flow time of the batch of material in a device and a pipe based on a detection result of the detection device and an operation status of the system. The operation status of the system refers to a status of the system during the production process, which may be represented by relevant parameters during the production process of the system, for example, a working power of the system, a material transportation rate, etc. The flow time refers to a time when the material is placed in a device or a time when the material flows through a pipe, for example, a material emptying time (in a device), etc. In some embodiments, the system may adjust a moment at which the material begins to be emptied and a moment at which the material begins to be transported based on the predicted result. For example, the first reactor 1 starts to be emptied at 9:55 AM, it is predicted that it will take 5 minutes for the material to be emptied, and a transportation time for the material to enter the first reactor 1 is 1 minute, so it may start dosing the material into the first reactor 1 at 9:59 AM without waiting for the first reactor 1 to be completely emptied.

In some embodiments, a predicted material emptying time may satisfy a following condition: the predicted material emptying time=a total amount of the material/a material emptying rate.

In some embodiments, in order to determine the moment at which the material begins to be transported, it is necessary to determine transport data. The transport data refers to data related to material transportation. In some embodiments, the transportation data may satisfy a following condition: the transportation data=a total amount of the material/the material transportation rate.

In some embodiments, the detection device may be arranged at other locations in the system, such as a connection between the second reactor 2 and the discharge pipe 8 or in the second reactor 2, and configured to detect an amount of the material at a moment the material starts to be discharged from the second reactor 2.

In some embodiments, by providing the detection device, idle time spent waiting for emptying can be reduced, thereby improving the efficiency.

In some embodiments, the detection device may include a concentration detection device (not shown in the figure). The concentration detection device may be configured to detect a concentration of the cellulosic ethanol. In some embodiments, the concentration detection device may be arranged in the ethanol pipe 10.

In some embodiments, the system may determine a count of the circulation of the material in the first reactor 1 and the second reactor 2 based on the concentration of the cellulosic ethanol detected by the concentration detection device. For example, when the detected concentration of the cellulosic ethanol is below a preset threshold, the circulation of the material in the first reactor 1 and the second reactor 2 may be ended.

In some embodiments, the concentration of produced cellulosic ethanol being below a preset threshold indicates that raw material is no longer able to be produced into the cellulosic ethanol or the concentration of the produced cellulosic ethanol is extremely low. At this time, the circulation of enzymatic hydrolysis and fermentation is ended, which may save time and resources.

In some embodiments, the system may include a temperature control system (not shown in the figure). The temperature control system may be configured to control a steam transportation rate when heating/holding, thus enabling temperature control of the coil insulation device 13 and the insulation layer 12. In some embodiments, the temperature control system may include a processor arranged in the first reactor 1, a temperature sensor, a valve controlling steam entering/exiting the hot water tank 5, and a steam flow rate sensor.

In some embodiments, the hot water tank 5 may be heated by high-temperature steam. The high-temperature steam may enter the hot water tank 5 through an inlet of a hot water pipe of the hot water tank 5, heat water in the hot water tank 5, and the steam is condensed and discharged, so that the water in the hot water tank 5 is transported to the coil insulation device 13 and the insulation layer 12. In some embodiments, the temperature control system may control a steam transportation rate to achieve accurate control of a temperature. For example, the temperature control system may control the temperature by predicting a future steam transportation rate.

In some embodiments, the temperature control system may determine the future steam transportation rate based on a historical temperature, a historical pressure, a historical steam flow rate, and a preset temperature through a vector database or a preset algorithm etc. In some embodiments, the temperature control system may determine the future steam transportation rate based on a steam transportation rate prediction model.

In some embodiments, the steam transportation rate prediction model is a model for determining the steam transportation rate. In some embodiments, the steam transportation rate prediction model may be a machine learning model. In some embodiments, the steam transportation rate prediction model may be a Recurrent Neural Network (RNN), etc.

In some embodiments, an input of the steam transportation rate prediction model is the historical temperature, the historical pressure, the historical steam flow rate, and the preset temperature, and an output of the steam transportation rate prediction model is the steam transportation rate at a future time point. The historical may include a current moment. Each input feature of the steam transportation rate prediction model may be a feature sequence composed of features at multiple time points.

In some embodiments, the steam transportation rate prediction model may be obtained based on a plurality of labeled training samples. For example, each of the plurality of labeled training samples may be inputted into an initial steam transportation rate prediction model. A loss function may be constructed based on the label of the labeled training sample and an output result of the initial steam transportation rate prediction model. A parameter of the initial steam transportation rate prediction model may be iteratively updated by gradient descent or other techniques based on the loss function. The model training is completed when a preset condition is met, and a trained steam transportation rate prediction model is obtained. The preset condition may be a convergence of the loss function, a count of iterations reaching a threshold, etc. In some embodiments, each of the training samples includes a sample historical temperature, a sample historical pressure, a sample historical steam flow rate, and a sample preset temperature and is labeled with the steam transportation rate. In some embodiments, the training samples may be obtained from historical data. The label of a training sample may be obtained by automatic labeling the training sample a time points. For example, temperature, pressure, and steam transportation rate at a 5 s, 10 s, 15 s, and 20 s are recorded, the temperature, pressure, and steam transportation rates at the 5 s, 10 s, and 15 s are used as the sample historical temperature, sample historical pressure, and sample historical steam transportation rate, the temperature at the 20 s as the sample preset temperature, and the steam transportation rate at the 20 s as the label.

In some embodiments, the temperature control system may control the steam transportation rate by predicting the future steam transportation rate, thereby achieving the accurate control of the temperature.

In some embodiments, the temperature control system may also be configured to preheat and precool the first reactor 1. For example, before the first reactor 1 is fed with material for the first time, the temperature control system may preheat the first reactor 1 to reach a preset reaction temperature in advance. As another example, due to an inconsistency between an evaporation temperature and the enzymatic hydrolysis temperature, the temperature control system may preheat or precool the reactor 1 correspondingly in advance based on a current temperature and an actual temperature before the material is added. The precooling refers to stopping heating to allow the first reactor 1 to start cooling down.

Some embodiments of the present disclosure provide a method (also referred to as a cellulosic ethanol production method) for producing cellulosic ethanol by biomass saccharification and fermentation using the system (e.g., the system 100, the system 200) (also referred to as a cellulosic ethanol production system) for producing cellulosic ethanol by biomass saccharification and fermentation. The method includes a dosing step, an enzymatic hydrolysis reaction step, a fermentation reaction step, a cellulosic ethanol production step, and repeat steps.

In the dosing step, the biomass feedstock is added to a citric acid buffer solution, and then cellulase is added to from a mixture. Further, the prepared mixture is dosed to the first reactor 1 through the enzymatic hydrolysis dosing pipe 11.

In the enzymatic hydrolysis reaction step, the mixture is carried out an enzymatic hydrolysis reaction by maintaining a temperature of the first reactor 1 at an enzymatic hydrolysis reaction temperature through the insulation layer 12.

In the fermentation reaction step, the material (i.e., the mixture) after the enzymatic hydrolysis reaction in the first reactor 1 is transported to the second reactor 2 through the fermentation pipe 6, and then fermentation strains are added to the second reactor through the fermentation dosing pipe 21. Further, the material after the enzymatic hydrolysis reaction is carried out a fermentation reaction by maintaining a temperature of the second reactor 2 at a fermentation temperature.

In the cellulosic ethanol production step, after the fermentation reaction is completed, the material after the fermentation reaction in the second reactor 2 is transported to the first reactor 1 through the discharge pipe 8. The cellulosic ethanol in the material after the fermentation reaction is evaporated into cellulosic ethanol vapors in the first reactor, and the cellulosic ethanol vapors flow into the collection tank 4 through the ethanol pipe 10 and are condensed into the cellulosic ethanol.

In the repeat steps, the enzymatic hydrolysis reaction step, the fermentation reaction step, and the cellulosic ethanol production step are repeated. The material is respectively circulated multiple cycles in the first reactor 1 and the second reactor 2, and after the circulation is completed in the second reactor 2, the material is discharged from the system through the first discharge pipe 16.

In some embodiments, the cellulosic ethanol production method corresponds to a single-circulation flow of a same batch of biomass feedstock between the first reactor 1 and the second reactor 2, and the material may be circulated 4 to 6 cycles in the first reactor 1 and the second reactor 2.

In some embodiments, the cellulosic ethanol production system further includes the storage tank 3 arranged on the discharge pipe 8, the third diaphragm pump 17, and the second discharge pipe 18. In such cases, the cellulosic ethanol production method includes a dosing step, an enzymatic hydrolysis reaction step, a fermentation reaction step, a storage step, a cellulosic ethanol production step, and repeat steps.

In the dosing step, the biomass feedstock is added to a citric acid buffer solution, and then cellulase is added to from a mixture. Further, the prepared mixture is dosed to the first reactor 1 through the enzymatic hydrolysis dosing pipe 11.

In the enzymatic hydrolysis reaction step, the mixture is carried out an enzymatic hydrolysis reaction by maintaining a temperature of the first reactor 1 at an enzymatic hydrolysis reaction temperature through the insulation layer 12.

In the fermentation reaction step, the material (i.e., the mixture) after the enzymatic hydrolysis reaction in the first reactor 1 is transported to the second reactor 2 through the fermentation pipe 6, and then fermentation strains are added to the second reactor through the fermentation dosing pipe 21. Further, the material after the enzymatic hydrolysis reaction is carried out a fermentation reaction by maintaining a temperature of the second reactor 2 at a fermentation temperature.

In the storage step, the material after the fermentation reaction in the second reactor 2 is transported to the storage tank 3.

After the material after the enzymatic hydrolysis reaction in the first reactor has been emptied, the dosing step and the enzymatic hydrolysis reaction step are repeated.

After the material after the fermentation reaction in the second reactor 1 has been emptied, the fermentation reaction step is repeated to transport the material after the enzymatic hydrolysis reaction in the first reactor 1 to the second reactor 2 through the fermentation pipe 6 to carry out the fermentation reaction.

In the cellulosic ethanol production step, after the material after the enzymatic hydrolysis reaction in the first reactor 1 has been emptied, the material after the fermentation reaction in the storage tank 3 is transported to the first reactor 1 through the discharge pipe 8. The cellulosic ethanol in the material after the fermentation reaction is evaporated into the cellulosic ethanol vapors in the first reactor 1, and the cellulosic ethanol vapors are transported into the collection tank 4 through the ethanol pipe 10 and are condensed into the cellulosic ethanol.

After the material after the fermentation reaction in the storage tank 3 has been emptied, the storage step, the enzymatic hydrolysis reaction step, the fermentation reaction step, and the cellulosic ethanol production step are repeated. The material is circulated multiple cycles in the first reactor 1, the second reactor 2, and the storage tank 3, and after the circulation is completed in the second reactor 2, the material is discharged from the system through the first discharge pipe 16.

In some embodiments, the cellulosic ethanol production method corresponds to a double-circulation flow of two batches of biomass material between the first reactor 1 and the second reactor 2, and the material may be circulated 4 to 6 cycles in the first reactor 1, the second reactor 2, and the storage tank 3.

In some embodiments, in the cellulosic ethanol production method, a certain concentration of hydrolysis product (i.e., fermentable glucose) is accumulated and fermented to produce the cellulosic ethanol, thereby addressing the issue of the activity inhibition of the cellulase caused by the glucose accumulation. In addition, by combining the cellulose hydrolysis process, the fermentation process, and the ethanol extraction process, these three processes are combined into a cyclic process in which the biomass feedstock are subjected to multiple cycles of the enzymatic saccharification, the fermentation, and the ethanol extraction at intervals, which reduces the inhibition of ethanol accumulation on the hydrolysis and fermentation processes, thereby increasing the conversion rate of the cellulosic ethanol.

In some embodiments, in the dosing step, a content of the biomass feedstock is 15%~20% of a dry substrate, a concentration of the citric acid buffer solution is 0.1 mol/L, a pH of the citric acid buffer solution is 5.0~6.0, and a content of the cellulase is 4%~6% of the dry substrate. In some embodiments, the content of the biomass feedstock, the concentration and pH of the citric acid buffer solution, and the content of the cellulase in the dosing step are applicable for both the single-circulation approach and the double-circulation approach mentioned above.

In some embodiments, in the enzymatic hydrolysis reaction step, a duration of the enzymatic hydrolysis reaction is 10 h~14 h. In some embodiments, the duration of the enzymatic hydrolysis reaction is applicable for both the single-circulation approach and the double-circulation approach mentioned above.

In some embodiments, in the fermentation reaction step, a mass ratio of the added fermentation strains is 0.1%~1%, and a duration of the fermentation reaction is 10 h~14 h. In some embodiments, the mass ratio of the added fermentation strains and the duration of the fermentation reaction are applicable for both the single-circulation approach and the double-circulation approach mentioned above.

In some embodiments, in repeating the enzymatic hydrolysis reaction step, the fermentation reaction step, and the cellulosic ethanol production step, the same batch of material may be circulated for 4 to 6 cycles in the first reactor 1 and the second reactor 2, respectively.

In some embodiments, two batches of material may be circulated for 4 to 6 times in the first reactor 1, the second reactor 2, and the storage tank 3 until the circulation are completed in the second reactor 2, and the material is discharged from the system through the first discharge pipe 16.

In some embodiments, the cellulase may be Cellic CTec 2. In some embodiments, the cellulase is applicable for both the single-circulation approach and the double-circulation approach mentioned above.

In some embodiments, by controlling the amount of reactants added and the reaction conditions, the progress of the reaction may be precisely controlled, which is conducive to the full progress of the reaction, while avoiding the waste of the material and energy, thereby improving the conversion rate of the product.

In some embodiments, the enzymatic hydrolysis reaction temperature is a highest temperature at which a survival rate of the fermentation strains is above 80%. In some embodiments, the enzymatic hydrolysis reaction temperature is applicable for both the single-circulation approach and the double-circulation approach mentioned above. In some embodiments, the enzymatic hydrolysis reaction temperature may be set higher or lower as desired, and the enzymatic hydrolysis reaction temperature can be set to improve the survival rate of the fermentation strains.

In some embodiments, the enzymatic hydrolysis reaction temperature may be determined by preparing a test system by using the citric acid buffer solution, adding glucose and the fermentation strains in the test system, incubating the test system for a preset time period at multiple temperatures ranging from 40° C. to 50° C., respectively, for the test system incubated at each of the multiple temperatures, determining a count of viable bacteria of the fermentation strains, and determining the enzymatic hydrolysis reaction temperature based on a survival rate of the viable bacteria after the preset time period in the test system incubated at each of the multiple temperatures.

In some embodiments, the enzymatic hydrolysis reaction temperature may be determined by preparing the test system by using the citric acid buffer solution with a concentration of 0.1 mol/L, adding the glucose with a concentration of 100 g/L and the fermentation strains with a mass ratio of 1% in the test system, incubating the test system for 12 h at 40° C., 41° C., 42° C., 43° C., 44° C., 45° C., 46° C., 47° C., 48° C., 49° C., 50° C., respectively, for the test system incubated at each of the 40° C., 41° C., 42° C., 43° C., 44° C., 45° C., 46° C., 47° C., 48° C., 49° C., and 50° C., measuring the count of the viable bacteria of the fermentation strains using a plate counting technique, and selecting a highest temperature at which the survival rate of the viable bacteria is 80% after the 12 hours of incubation as the enzymatic hydrolysis reaction temperature.

In some embodiments, based on multiple sets of experimental data that have been tested, an optimal enzymatic hydrolysis reaction temperature may be determined by a preset algorithm. For example, the optimal enzymatic hydrolysis reaction temperature may be determined by determining a reaction temperature at which the survival rate of the viable bacteria is highest in the multiple sets of experimental data as the optimal enzymatic hydrolysis reaction temperature.

In some embodiments, based on the multiple sets of experimental data that have been tested, the optimal enzymatic hydrolysis reaction temperature may be determined by an enzymatic hydrolysis reaction temperature determination model. Each set of the multiple sets of experimental data may include an experimental temperature, an experimental pressure, a strain type, features of a culture system (a buffer solution type, a concentration, a strain mass ratio, etc.), survival rates of viable bacteria at multiple moments, etc.

In some embodiments, the enzymatic hydrolysis reaction temperature determination model is a model for determining the optimal enzymatic hydrolysis reaction temperature. In some embodiments, the enzymatic hydrolysis reaction temperature determination model may be a machine learning model. The enzymatic hydrolysis reaction temperature determination model may be a Recurrent Neural Network (RNN), etc.

In some embodiments, the enzymatic hydrolysis reaction temperature determination model includes a feature extraction layer and a temperature determination layer. An input of the feature extraction layer includes the multiple sets of experimental data and culture data. An output of the feature extraction layer is feature data. An input of the temperature determination layer is the feature data, and an output of the temperature determination layer is a predicted optimal enzymatic hydrolysis reaction temperature. The culture data includes culture composition, pH, etc.

In some embodiments, the enzymatic hydrolysis reaction temperature determination model may be obtained based on a plurality of labeled training samples. For example, each of the plurality of labeled training samples may be inputted into an initial enzymatic hydrolysis reaction temperature determination model. A loss function may be constructed based on the label of the labeled training sample and an output result of the initial enzymatic hydrolysis reaction temperature determination model. A parameter of the initial enzymatic hydrolysis reaction temperature determination model may be updated iteratively by gradient descent or other techniques based on the loss function. The model training is completed when a preset condition is satisfied, and a trained enzymatic hydrolysis reaction temperature determination model is obtained. The preset condition may be a convergence of the loss function, a count of iterations reaching a threshold, etc. In some embodiments, each of the training samples includes sample multiple sets of experimental data, sample culture data, and the label of the training sample is labeled with the optimal enzymatic hydrolysis reaction temperature corresponding to the training sample. The training samples may be obtained from historical experimental data. The labels may be obtained by manual labeling. For example, multiple sample determination experiments (sample experimental pressures, sample strain types, sample features of the culture system) are performed on a training sample, i.e., the training sample are incubated with viable bacteria at different temperatures, and a temperature with a highest survival rate of viable bacteria is determined as the optimal enzymatic hydrolysis reaction temperature corresponding to the training sample.

In some embodiments, a span of experimental temperatures in the sample determination experiments may be different from a span of experimental temperatures of the model input. For example, a set of experimental temperatures for the model input may be (40° C., 41° C., 42° C. . . . ) with a span of 1° C., and a set of experimental temperatures for the sample may be (40.5° C., 41° C., 41.5° C.) with a span of 0.5° C. That is, the span of the experimental temperatures in the sample determination experiments is more small.

In some embodiments, the experimental data may be determined based on historical data and existing information. For example, for strains whose optimal temperature range may be found through retrieval, the retrieved temperature range may be used directly as the range for the experiments. Conversely, for strains whose optimal temperature range cannot be found through retrieval, the experimental temperature range may be determined based on historical data. For example, according to the type of the target strain, strains similar to the target strain (e.g., both belong to thermophilic bacteria or mesophilic bacteria) may be searched for, and the experimental temperature range may be determined based on the historical data of the similar strains.

In some embodiments, multiple experimental temperatures in the multiple sets of experimental data input to the model may be determined based on how close the predicted optimal enzymatic hydrolysis reaction temperature is to the historical data. For example, in a scenario A, experiments are conducted at 40° C., 41° C., 42° C., 43° C., and 44° C., and accordingly, five sets of experimental results are obtained; in a scenario B, experiments are conducted at 41° C., 42° C., 43° C., 44° C., and 45° C., and accordingly, five sets of experimental results are obtained. The scenario A and the scenario B are Input into the enzymatic hydrolysis reaction temperature determination model to obtain the predicted optimal enzymatic hydrolysis reaction temperatures for scenario A and scenario B. A scenario of the scenario A and the scenario B which has the closest predicted optimal enzymatic hydrolysis reaction temperature to the historical data is selected as the experimental data input to the model.

In some embodiments, multiple experimental temperatures in the multiple sets of experimental data input to the model may be determined based on prediction accuracy of the enzymatic hydrolysis reaction temperatures at different experimental temperatures.

The prediction accuracy refers to a frequency of the occurrence of the optimal enzymatic hydrolysis reaction temperature among multiple prediction results. If the frequency of the occurrence of a specific optimal enzymatic hydrolysis reaction temperature is high, the experimental data that includes this reaction temperature t is advisable to select as the experimental data input into the model. The prediction accuracy may be obtained by statistical analysis of the historical data. For example, based on the historical data, in the 100 predictions, average prediction accuracy of the experimental data containing 42° C. in the input of the model is 95% (i.e., the frequency of the occurrence of the optimal enzymatic hydrolysis reaction temperature 42° C. is 95 times), and accordingly, 42° C. is the temperature that needs to be tested. The prediction accuracy of the enzymatic hydrolysis reaction temperature being high indicates that the experimental data corresponding to the enzymatic hydrolysis reaction temperature can provide a lot of information and contributes to the accurate prediction of the final optimal enzymatic hydrolysis reaction temperature.

In some embodiments, a plurality of experiment temperatures with high historical prediction accuracy are sequentially determined to construct an experimental plan as a final experimental plan. Experiments are conducted based on the experimental plan to obtain the multiple sets of experimental data, which are then input to the model for prediction.

In some embodiments, a plurality of temperatures with the highest prediction accuracy (e.g., 10) may be determined directly as the experimental temperatures.

In some embodiments, the optimal enzymatic hydrolysis reaction temperature is determined through the enzymatic hydrolysis reaction temperature determination model, so that a more accurate optimal enzymatic hydrolysis reaction temperature can be obtained. Moreover, compared with direct experiment, the use of the model can significantly reduce the count of experiments, effectively reduce costs, and effectively save time and experimental resources.

The following embodiments are provided to further illustrate the system and method for producing cellulosic ethanol by biomass saccharification and fermentation in the present disclosure.

Embodiment 1

Validation experiment of the inhibitory effect of glucose and ethanol on the enzymatic hydrolysis reaction.

A reaction system was prepared using a citric acid buffer solution with a concentration of 0.1 mol/L. The citric acid buffer solution was added to a corn cob waste system in which a content of the biomass feedstock was 15% of a dry substrate, a pH of the mixture was maintained at 5.0~6.0, and cellulase Cellic CTec 2 with a content of 4% of the dry substrate was added to the mixture to prepare three groups of 1 L reaction systems.

| Groups | Externally added inhibitor |
|---|---|
| A | None |
| B | 100 g/L glucose |
| C | 50 g/L ethanol |

Figure 3:
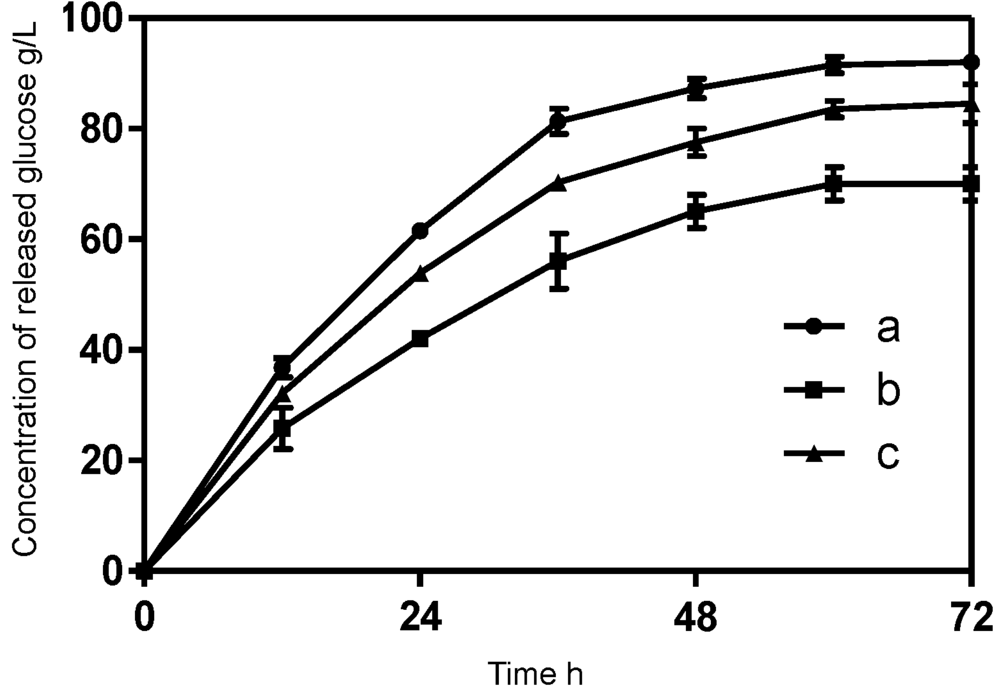
FIG. 3 is a schematic diagram illustrating that glucose release concentration changes over time in an enzymatic hydrolysis system with external addition of glucose and ethanol according to some embodiments of the present disclosure.

The three reaction systems were subjected to enzymatic hydrolysis at 50° C. for 72 hours under a condition of stirring at 300 rpm. Samples were taken from each reaction system every 12 hours to measure an amount of glucose released by the enzymatic hydrolysis, and results are shown in FIG. 3. FIG. 3 is a schematic diagram illustrating that glucose release concentration changes over time in an enzymatic hydrolysis system with external addition of glucose and ethanol according to some embodiments of the present disclosure.

Experimental conclusion: both glucose and ethanol have certain inhibitory effects on the enzymatic hydrolysis of cellulose. After 100 g/L of glucose was added to Group B, the amount of glucose released during the 72-hour enzymatic hydrolysis was 24% lower than that of the control Group A without inhibitor. After 50 g/L of ethanol was added to Group C, the amount of glucose released during the 72-hour enzymatic hydrolysis was 8% lower than that of the control Group A.

Embodiment 2

A heat resistance experiment was carried out on Angel brewing yeast and *Zymomonas mobilis* to determine the enzymatic hydrolysis reaction temperature T.

The method in the present disclosure is applicable to a variety of ethanol fermentation strains. This experiment is illustrated by taking two common ethanol fermentation strains: Angel brewing yeast and *Zymomonas mobilis* as examples.

Figure 4:
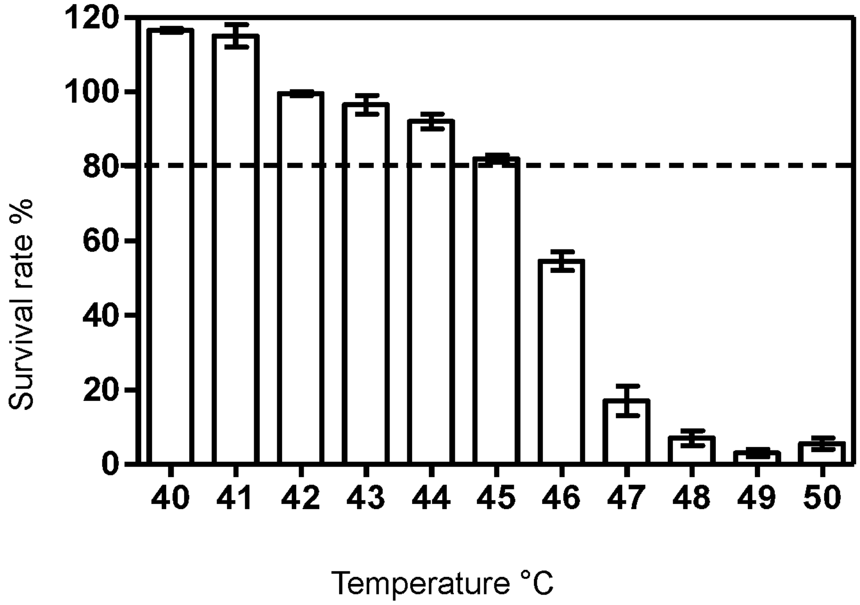
FIG. 4 is a columnar schematic diagram illustrating survival rates of brewing yeast under different temperatures in a heat resistance experiment according to some embodiments of the present disclosure.
Figure 5:
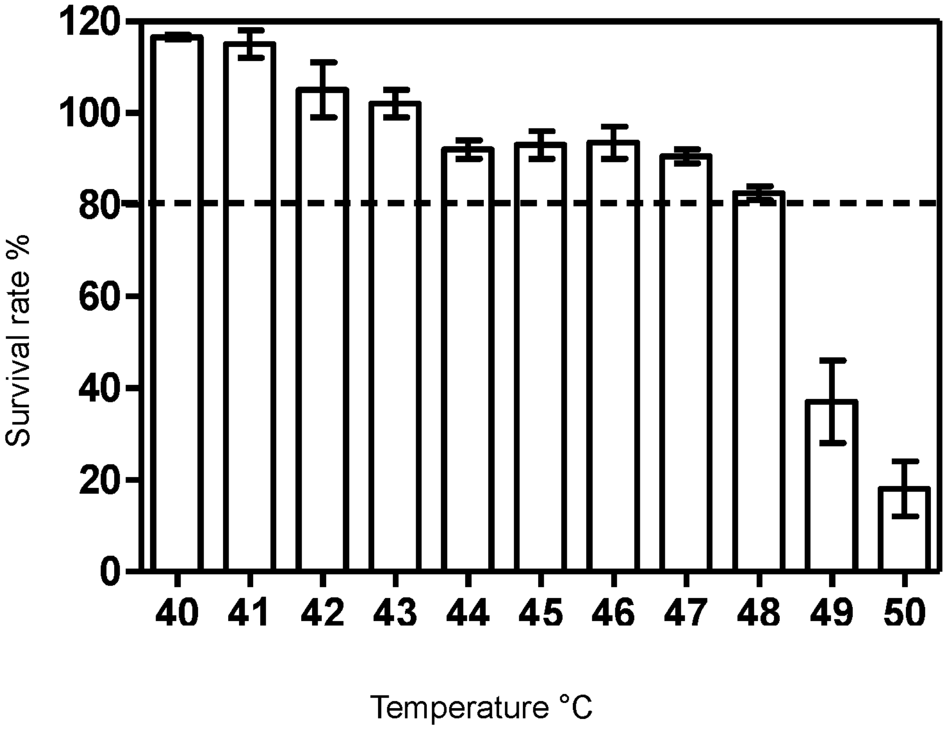
FIG. 5 is a columnar schematic diagram illustrating survival rates of *Zymomonas mobilis* under different temperatures in a heat resistance experiment according to some embodiments of the present disclosure.

A 100 g/L glucose solution was prepared using a citric acid buffering solution. The solution was divided into two portions. One portion was mixed with 1% mass concentration of Angel brewing yeast powder, and the other portion was mixed with 1% mass concentration of *Zymomonas mobilis* bacteria liquid. Samples were then taken from each portion. The samples were incubated at different temperatures (multiple temperatures within the range of 40° C.~50° C., with an interval of 1 degree between adjacent temperatures) for 12 hours. For the sample incubated at each temperature, a count of viable bacteria before and after the incubation was measured using a plate counting technique, and a change in the count of viable bacteria before and after incubation was determined, and results are shown in FIG. 4 and FIG. 5. FIG. 4 is a columnar schematic diagram illustrating survival rates of a brewing yeast under different temperatures in a heat resistance experiment according to some embodiments of the present disclosure. FIG. 5 is a columnar schematic diagram illustrating survival rates of *Zymomonas mobilis* under different temperatures in a heat resistance experiment according to some embodiments of the present disclosure.

Experimental conclusion: through statistical analysis, after 12 hours of incubation, a highest temperature at which a survival rate of the fermentation strains is above 80% was selected as the enzymatic hydrolysis reaction temperature T. The enzymatic hydrolysis reaction temperature T corresponding to the Angel brewing yeast was 45° C., and the enzymatic hydrolysis reaction temperature T corresponding to the *Zymomonas mobilis* was 48° C.

Embodiment 3

A first single-circulation embodiment of the cellulosic ethanol production method in the present disclosure includes steps 110-170.

In step 110, the enzymatic hydrolysis reaction temperature T was determined according to the above Embodiment 2.

In step 120, material of the reaction system was prepared by adding corn cob waste with a dry substrate content of 15 kg (w/w) to an aqueous solution containing a citric acid buffer system to make the mixture reach 100 kg, a pH of the mixture was maintained at 5.0~6.0, 0.6 kg cellulase Cellic CTec 2 was added to the mixture, and the mixture was stirred evenly. Further, the prepared material was added into the first reactor through the enzymatic hydrolysis dosing pipe.

In step 130, a temperature of the first reactor was set to and maintained at 45° C., and the enzymatic hydrolysis reaction was carried out for 10-14 hours under stirring of 300 rpm.

In step 140, a temperature of the second reactor was set to 35° C. (an optimal fermentation temperature of the brewing yeast), after the material after the enzymatic hydrolysis reaction in step 130 was transported from the first reactor to the second reactor through the first diaphragm pump, 1 kg of Angel brewing yeast powder was inoculated into the second reactor through the fermentation dosing pipe of the second reactor, and the fermentation reaction was carried out for 10~14 hours under stirring of 100 rpm to complete a reaction cycle.

In step 150, after the material after the fermentation reaction in step 140 was transported from the second reactor to the first reactor, a second enzymatic hydrolysis reaction was carried out under constant stirring, and produced cellulosic ethanol was evaporated and collected in the collection tank.

In step 160, the material after the second enzymatic hydrolysis in step 150 was transported from the first reactor to the second reactor.

In step 170, steps 140 to 160 were repeated for 5 cycles. Finally, 4.4 kg of material in the collection tank was obtained, which contained 35% cellulosic ethanol, and the amount of the obtained cellulosic ethanol was 1.54 kg. Material in the second reactor was 89.5 kg, in which the cellulosic ethanol content was 3.1%, and the amount of the obtained cellulosic ethanol was 2.77 kg. A total amount of the obtained cellulosic ethanol was 4.31 kg, and a conversion rate of the cellulosic ethanol was 84.5%.

Embodiment 4

A second single-circulation embodiment of the cellulosic ethanol production method in the present disclosure includes steps 210-270.

In step 210, the enzymatic hydrolysis reaction temperature T was determined according to the above Embodiment 2.

In step 220, material of the reaction system was prepared by adding corn cob waste with a dry substrate content of 20 kg (w/w) to an aqueous solution containing a citric acid buffer system to make the mixture reach 100 kg, a pH of the mixture was maintained at 5.0~6.0, 0.8 kg cellulase Cellic CTec 2 was added to the mixture, and the mixture was stirred evenly. Further, the prepared material was added into the first reactor through the enzymatic hydrolysis dosing pipe.

In step 230, a temperature of the first reactor was set to and maintained at 45° C., and the enzymatic hydrolysis reaction was carried out for 10-14 hours under stirring of 300 rpm.

In step 240, a temperature of the second reactor was set to 35° C., after the material after the enzymatic hydrolysis reaction in step 230 was transported from the first reactor to the second reactor through the first diaphragm pump, 1 kg of Angel brewing yeast powder was inoculated into the second reactor through the fermentation dosing pipe of the second reactor, and the fermentation reaction was carried out for 10~14 hours under stirring of 100 rpm to complete a reaction cycle.

In step 250, after the material after the fermentation in step 240 was transported from the second reactor to the first reactor, a second enzymatic hydrolysis reaction was carried out under constant stirring, and produced cellulosic ethanol was evaporated and collected in the collection tank.

In step 260, the material after the second enzymatic hydrolysis in step 250 was transported from the first reactor to the second reactor.

In step 270, steps 240 to 260 were repeated for 6 cycles.

Finally, 4.7 kg of material in the collection tank was obtained, which contained 38% cellulosic ethanol, and the amount of the obtained cellulosic ethanol was 1.79 kg. Material in the second reactor was 90.5 kg, in which the cellulosic ethanol content was 4.1%, and the amount of the obtained cellulosic ethanol was 3.71 kg. A total amount of the obtained cellulosic ethanol was 5.50 kg, and a conversion rate of the cellulosic ethanol was 80.9%.

Embodiment 5

A third single-circulation embodiment of the cellulosic ethanol production method in the present disclosure includes steps 310-370.

In step 310, the enzymatic hydrolysis reaction temperature T was determined according to the above Embodiment 2.

In step 320, material of the reaction system was prepared by adding corn cob waste with a dry substrate content of 20 kg (w/w) to an aqueous solution containing a citric acid buffer system to make the mixture reach 100 kg, a pH of the mixture was maintained at 5.0~6.0, 0.8 kg cellulase Cellic CTec 2 was added to the mixture, and the mixture was stirred evenly. Further, the prepared material was added into the first reactor through the enzymatic hydrolysis dosing pipe.

In step 330, a temperature of the first reactor was set to and maintained at 48° C., and the enzymatic hydrolysis reaction was carried out for 10-14 hours under stirring of 300 rpm.

In step 340, a temperature of the second reactor was set to 35° C., after the material after the enzymatic hydrolysis reaction in step 330 was transported from the first reactor to the second reactor through the first diaphragm pump, 1 kg of activated *Zymomonas mobilis* bacteria liquid was inoculated into the second reactor through the fermentation dosing pipe of the second reactor, and the fermentation reaction was carried out for 10~14 hours under stirring of 100 rpm to complete a reaction cycle.

In step 350, after the material after the fermentation reaction in step 340 was transported from the second reactor to the first reactor, a second enzymatic hydrolysis reaction was carried out under constant stirring, and produced cellulosic ethanol was evaporated and collected in the collection tank.

In step 360, the material after the second enzymatic hydrolysis in step 350 was transported from the first reactor to the second reactor.

In step 370, steps 340 to 360 were repeated for 6 cycles.

Finally, 4.8 kg of material in the collection tank was obtained, which contained 39% cellulosic ethanol, and the amount of the obtained cellulosic ethanol was 1.87 kg. Material in the second reactor was 93.5 kg, in which the cellulosic ethanol content was 4.13%, and the amount of the obtained cellulosic ethanol was 3.86 kg. A total amount of the obtained cellulosic ethanol was 5.73 kg, and a conversion rate of the cellulosic ethanol was 84.3%.

Embodiment 6

A first double-circulation embodiment of the cellulosic ethanol production method in the present disclosure includes steps 410-480.

In step 410, the enzymatic hydrolysis reaction temperature T was determined according to the above Embodiment 2.

In step 420, a first batch of material of the reaction system was prepared by adding corn cob waste a dry substrate content of 20 kg (w/w) to an aqueous solution containing a citric acid buffer system to make the mixture reach 100 kg, a pH of the mixture was maintained at 5.0~6.0, 0.8 kg cellulase Cellic CTec 2 was added to the mixture, and the mixture was stirred evenly. Further, the prepared first batch of material was added into the first reactor through the enzymatic hydrolysis dosing pipe.

In step 430, a temperature of the first reactor was set to and maintained at 45° C., and the enzymatic hydrolysis reaction was carried out for 10-14 hours under stirring of 300 rpm.

In step 440, a temperature of the second reactor was set to 35° C., after the first batch of material after the enzymatic hydrolysis reaction in step 430 was transported from the first reactor to the second reactor through the first diaphragm pump, 1 kg of Angel brewing yeast powder was inoculated into the second reactor through the fermentation dosing pipe of the second reactor, and the fermentation reaction was carried out for 10~14 hours under stirring of 100 rpm to complete a reaction cycle of the first batch of material.

After the first batch of material was transported from the first reactor to the second reactor through the first diaphragm pump, a second batch of material of the reaction system was prepared according to the preparation manner in step 420, and the second batch of material of the reaction system was processed according to step 430, i.e., the second batch of material prepared according to step 420 was added to the first reactor through the enzymatic hydrolysis dosing pipe, and the enzymatic hydrolysis reaction was carried out for 10~14 hours under stirring of 300 rpm.

In step 450, the first batch of material in the second reactor was transported to the storage tank through the second diaphragm pump, and then the second batch of material in the first reactor was transported to the second reactor, and step 440 is performed on the second batch of material to complete a reaction cycle of the second batch of material.

In step 460, the first batch of material in the storage tank was transported to the first reactor through the discharge pipe and continuously stirred, and produced cellulosic ethanol was evaporated and collected in the collection tank, while the second batch of material was transported from the second reactor to the storage tank.

In step 470, the first batch of material was again transported from the first reactor to the second reactor. The second batch of material was always one container behind the first batch of material.

In step 480, steps 440-460 were repeated for 6 cycles.

Finally, 8.8 kg of material in the collection tank was obtained, which contained 38.5% cellulosic ethanol, and the amount of the obtained cellulosic ethanol was 3.39 kg. A total of 178.5 kg of the two batches of material were discharged, in which the cellulosic ethanol content was 4.2%, and the amount of the obtained cellulosic ethanol was 7.50 kg. A total amount of the obtained cellulosic ethanol was 10.85 kg, and a conversion rate of the cellulosic ethanol was 84.5%.

Embodiment 7

The enzymatic effect of the cellulosic ethanol production method in the present disclosure was compared with the enzymatic effect of the simultaneous saccharification and fermentation process.

Data in Embodiment 4 and Embodiment 5 was collected to calculate the ethanol conversion rate of the corn cob waste with 20% dry substrate according to the cellulosic ethanol production method in the present disclosure.

For the existing synchronous saccharification and fermentation process, corn cob waste with a dry substrate content of 20 kg (w/w) was added to an aqueous solution containing a citric acid buffer system to make the mixture reach 100 kg, a pH of the mixture was maintained at 5.0~6.0, 0.8 kg cellulase Cellic CTec 2 was added to the mixture, the mixture was stirred evenly, and 1 kg of Angel yeast powder was inoculated into the mixture. Under the stirring of 300 rpm, the mixture was reacted at 35° C. for 6 days to obtain 100.5 kg of material in which a content of the cellulosic ethanol was 5.2% and a conversion rate of the cellulosic ethanol was 76.9%.

Compared with the existing simultaneous saccharification and fermentation process, the conversion rate of cellulosic ethanol of the cellulosic ethanol production method in the present disclosure was increased from 76.9% to more than 80%, and the conversion rate improvement effect is obvious.

The basic concept has been described above, obviously, for those skilled in the art, the above detailed disclosure is only an example, and does not constitute a limitation to the present disclosure. Although not expressly stated here, those skilled in the art may make various modifications, improvements, and corrections to the present disclosure. Such modifications, improvements, and corrections are suggested in the present disclosure, so such modifications, improvements, and corrections still belong to the spirit and scope of the exemplary embodiments of the present disclosure.

Meanwhile, the present disclosure uses specific words to describe the embodiments of the present disclosure. For example, "one embodiment", "an embodiment", and/or "some embodiments" refer to a certain feature, structure, or characteristic related to at least one embodiment of the present disclosure. Therefore, it should be emphasized and noted that references to "one embodiment," "an embodiment" or "an alternative embodiment" two or more times in different places in the present disclosure do not necessarily refer to the same embodiment. In addition, certain features, structures, or characteristics in one or more embodiments of the present disclosure may be properly combined.

In some embodiments, counts describing the quantity of components and attributes are used. It should be understood that such counts used in the description of the embodiments use the modifiers "about", "approximately" or "substantially" in some examples. Unless otherwise stated, "about", "approximately" or "substantially" indicates that the stated figure allows for a variation of ±20%. Accordingly, in some embodiments, the numerical parameters used in the disclosure and claims are approximations that can vary depending on the desired characteristics of individual embodiments. In some embodiments, numerical parameters should consider the specified significant digits and adopt the general digit retention method. Although the numerical ranges and parameters used in some embodiments of the present disclosure to confirm the breadth of the range are approximations, in specific embodiments, such numerical values are set as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting effect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A system for producing cellulosic ethanol by biomass saccharification and fermentation, comprising:

- a first reactor configured to carry out an enzymatic hydrolysis reaction of a biomass feedstock;
- a second reactor configured to carry out a fermentation reaction of the biomass feedstock; and
- a collection tank configured to collect the cellulosic ethanol produced from the fermentation reaction of the biomass feedstock, wherein
  - the first reactor is provided with an enzymatic hydrolysis dosing pipe,
  - the second reactor is provided with a fermentation dosing pipe,
  - an outlet of the first reactor is connected to an inlet of the second reactor through a fermentation pipe,
  - an outlet of the second reactor is connected to an inlet of the first reactor through a discharge pipe;
  - a first discharge pipe is provided on the discharge pipe and configured to discharge material from the second reactor,
  - the first reactor is connected to an inlet of the collection tank through an ethanol pipe, and
  - the first reactor is provided with an insulation layer for heating and keeping the first reactor warm.

2. The system of claim 1, wherein the fermentation pipe is provided with a first diaphragm pump, and the discharge pipe is provided with a second diaphragm pump, the first discharge pipe being located downstream of the second diaphragm pump.

3. The system of claim 1, wherein a coil insulation device is provided at a connection between the first reactor and the ethanol pipe, and the coil insulation device and the insulation layer are respectively connected to a hot water tank through a hot water pipe, a centrifugal pump being provided on the hot water pipe.

4. The system of claim 1, wherein a storage tank, a third diaphragm pump, and a second discharge pipe are provided on the discharge pipe, the storage tank being located downstream of the first discharge pipe and configured to store material discharged from the second reactor, the second discharge pipe being located downstream of the third diaphragm pump.

5. The system of claim 1, wherein an ethanol freezing device is provided at a connection between an upper part of the collection tank and the ethanol pipe and configured to condense cellulosic ethanol vapors.

6. The system of claim 1, wherein a fermentation cooling device is provided outside the second reactor and configured to cool fermenting material inside the second reactor.

7. The system of claim 1, wherein a stirring device is respectively provided in the first reactor and the second reactor.

8. A method for producing cellulosic ethanol by biomass saccharification and fermentation, wherein the method is implemented by a system for producing cellulosic ethanol by biomass saccharification and fermentation, wherein the system comprises: a first reactor configured to carry out an enzymatic hydrolysis reaction of a biomass feedstock; a second reactor configured to carry out a fermentation reaction of the biomass feedstock; and a collection tank configured to collect the cellulosic ethanol produced from the fermentation reaction of the biomass feedstock, wherein the first reactor is provided with an enzymatic hydrolysis dosing pipe, the second reactor is provided with a fermentation dosing pipe, an outlet of the first reactor is connected to an inlet of the second reactor through a fermentation pipe, an outlet of the second reactor is connected to an inlet of the first reactor through a discharge pipe; a first discharge pipe is provided on the discharge pipe and configured to discharge material from the second reactor, the first reactor is connected to an inlet of the collection tank through an ethanol pipe, and the first reactor is provided with an insulation layer for heating and keeping the first reactor warm, and the method comprises:

in a dosing step, adding the biomass feedstock to a citric acid buffer solution, adding cellulase, and dosing the prepared mixture to the first reactor through the enzymatic hydrolysis dosing pipe;

in an enzymatic hydrolysis reaction step, carrying out the enzymatic hydrolysis reaction by maintaining a temperature of the first reactor at an enzymatic hydrolysis reaction temperature through the insulation layer;

in a fermentation reaction step, transporting the material after the enzymatic hydrolysis reaction in the first reactor to the second reactor through the fermentation pipe, adding fermentation strains to the second reactor through the fermentation dosing pipe, and carrying out the fermentation reaction on the material after the enzymatic hydrolysis reaction by maintaining a temperature of the second reactor at a fermentation temperature;

in a cellulosic ethanol production step, after completing the fermentation reaction, transporting the material after the fermentation reaction in the second reactor to the first reactor through the discharge pipe, wherein the cellulosic ethanol in the material after the fermentation reaction is evaporated into cellulosic ethanol vapors in the first reactor, and the cellulosic ethanol vapors flow into the collection tank through the ethanol pipe and are condensed into the cellulosic ethanol; and in repeat steps, repeating the enzymatic hydrolysis reaction step, the fermentation reaction step, and the cellulosic ethanol production step, wherein the material is respectively circulated multiple cycles in the first reactor and the second reactor, and after the circulation is completed in the second reactor, the material is discharged from the system through the first discharge pipe.

9. The method of claim 8, wherein in the dosing step, a content of the biomass feedstock is 15%~20% of a dry substrate, a concentration of the citric acid buffer solution is 0.1 mol/L, a pH of the citric acid buffer solution is 5.0~6.0, and a content of the cellulase is 4%~6% of the dry substrate;

in the enzymatic hydrolysis reaction step, a duration of the enzymatic hydrolysis reaction is 10 h~14 h; and/or in the fermentation reaction step, a mass ratio of the added fermentation strains is 0.1%~1%, and a duration of the fermentation reaction is 10 h~14 h.

10. The method of claim 8, wherein in the repeat steps, a same batch of the material is respectively circulated in the first reactor and the second reactor for 4 to 6 cycles.

11. The method of claim 8, wherein the enzymatic hydrolysis reaction temperature is a highest temperature at which a survival rate of the fermentation strains is above 80%.

12. The method of claim 8, wherein the enzymatic hydrolysis reaction temperature is determined by:

preparing a test system by using the citric acid buffer solution;

adding glucose and the fermentation strains in the test system;

incubating the test system for a preset time period at multiple temperatures ranging from 40° C. to 50° C., respectively;

for the test system incubated at each of the multiple temperatures, determining a count of viable bacteria of the fermentation strains; and determining the enzymatic hydrolysis reaction temperature based on a survival rate of the viable bacteria after the preset time period in the test system incubated at each of the multiple temperatures.

13. The method of claim 8, wherein the cellulase is Cellic CTec 2.

14. A method for producing cellulosic ethanol by biomass saccharification and fermentation, wherein the method is implemented by a system for producing cellulosic ethanol by biomass saccharification and fermentation, wherein the system comprises: a first reactor, a second reactor, a collection tank, a storage tank, a third diaphragm pump, and a second discharge pipe, wherein the first reactor is configured to carry out an enzymatic hydrolysis reaction of a biomass feedstock; the second reactor is configured to carry out a fermentation reaction of the biomass feedstock; and the collection tank configured to collect the cellulosic ethanol produced from the fermentation reaction of the biomass feedstock, wherein the first reactor is provided with an enzymatic hydrolysis dosing pipe, the second reactor is provided with a fermentation dosing pipe, an outlet of the first reactor is connected to an inlet of the second reactor through a fermentation pipe, an outlet of the second reactor is connected to an inlet of the first reactor through a discharge pipe; a first discharge pipe is provided on the discharge pipe and configured to discharge material from the second reactor, the first reactor is connected to an inlet of the collection tank through an ethanol pipe, the first reactor is provided with an insulation layer for heating and keeping the first reactor warm, the storage tank is provided on the discharge pipe, the storage tank is located downstream of the first discharge pipe for storing the material discharged from the second reactor, and the second discharge pipe is located downstream of the third diaphragm pump; and the method comprises:

in a dosing step, adding the biomass feedstock to a citric acid buffer solution, adding cellulase, and dosing the prepared mixture to the first reactor through the enzymatic hydrolysis dosing pipe;

in an enzymatic hydrolysis reaction step, carrying out the enzymatic hydrolysis reaction by maintaining a temperature of the first reactor at an enzymatic hydrolysis reaction temperature through the insulation layer;

in a fermentation reaction step, transporting the material after the enzymatic hydrolysis reaction in the first reactor to the second reactor through the fermentation pipe, adding fermentation strains to the second reactor through the fermentation dosing pipe, and carrying out the fermentation reaction on the material after the enzymatic hydrolysis reaction by maintaining a temperature of the second reactor at a fermentation temperature;

in a storage step, transporting the material after the fermentation reaction in the second reactor to the storage tank;

after the material after the enzymatic hydrolysis reaction in the first reactor has been emptied, repeating the dosing step and the enzymatic hydrolysis reaction step;

after the material after the fermentation reaction in the second reactor has been emptied, repeating the fermentation reaction step to transport the material after the enzymatic hydrolysis reaction in the first reactor to the second reactor through the fermentation pipe to carry out the fermentation reaction;

in a cellulosic ethanol production step, after the material after the enzymatic hydrolysis reaction in the first reactor has been emptied, transporting the material after the fermentation reaction in the storage tank to the first reactor through the discharge pipe, wherein the cellulosic ethanol in the material after the fermentation reaction is evaporated into cellulosic ethanol vapors in the first reactor, and the cellulosic ethanol vapors are transported into the collection tank through the ethanol pipe and are condensed into the cellulosic ethanol; and after the material after the fermentation reaction in the storage tank has been emptied, repeating the storage step, the enzymatic hydrolysis reaction step, the fermentation reaction step, and the cellulosic ethanol production step, wherein the material is respectively circulated multiple cycles in the first reactor, the second reactor, and the storage tank, and after the circulation is completed in the second reactor, the material is discharged from the system through the first discharge pipe.

15. The method of claim 14, wherein in the dosing step, a content of the biomass feedstock is 15%~20% of a dry substrate, a concentration of the citric acid buffer solution is 0.1 mol/L, a pH of the citric acid buffer solution is 5.0~6.0, and a content of the cellulase is 4%~6% of the dry substrate;

in the enzymatic hydrolysis reaction step, a duration of the enzymatic hydrolysis reaction is 10 h~14 h; and/or in the fermentation reaction step, a mass ratio of the added fermentation strains is 0.1%~1%, and a duration of the fermentation reaction is 10 h~14 h.

16. The method of claim 14, wherein the material is circulated in the first reactor, the second reactor, and the storage tank for 4 to 6 cycles.

17. The method of claim 14, wherein the enzymatic hydrolysis reaction temperature is a highest temperature at which a survival rate of the fermentation strains is above 80%.

18. The method of claim 14, wherein the enzymatic hydrolysis reaction temperature is determined by:

preparing a test system by using the citric acid buffer solution;

adding glucose and the fermentation strains in the test system;

incubating the test system for a preset time period at multiple temperatures ranging from 40° C. to 50° C., respectively;

for the test system incubated at each of the multiple temperatures, determining a count of viable bacteria of the fermentation strains; and determining the enzymatic hydrolysis reaction temperature based on a survival rate of the viable bacteria after the preset time period in the test system incubated at each of the multiple temperatures.

19. The method of claim 14, wherein the cellulase is Cellic CTec 2.

* * * * *